United States Patent [19]

Holmes et al.

[11] Patent Number: 5,347,125
[45] Date of Patent: Sep. 13, 1994

[54] MASS SPECTROMETER HAVING MEANS FOR OBSERVING THE RADIATION EMITTED WHEN IONS COLLIDE WITH A TARGET GAS

[75] Inventors: John L. Holmes, Ottawa; Alexander A. Mommers, Vanier, both of Canada

[73] Assignee: Fisons plc, Ipswich, England

[21] Appl. No.: 68,743

[22] Filed: May 28, 1993

[30] Foreign Application Priority Data

May 29, 1992 [GB] United Kingdom ............. 9211458.6

[51] Int. Cl.$^5$ .................. B01D 59/44; H01J 49/00
[52] U.S. Cl. ................................... 250/281
[58] Field of Search .................. 250/281, 282, 251

[56] References Cited

U.S. PATENT DOCUMENTS

| | | | |
|---|---|---|---|
| 4,536,652 | 8/1985 | Cooks et al. | 250/281 |
| 4,620,095 | 10/1986 | Miziolek | 250/281 |
| 4,861,987 | 8/1989 | Devienne | 250/281 |
| 4,866,267 | 9/1989 | Matsuda et al. | 250/281 |

OTHER PUBLICATIONS

Leventhal, Gas Phase Ion Chem, 1984, vol. 3, Ed. Bowers, Academic Press, pp. 309-355.
Hatada, Fujita et al, JAERI Issue 5026, pp. 1-5.
Johnson, Zare, Rostas, Leach, J. Chem. Phys. 1984, vol. 80 (6) pp. 2407-2428.
Donnelly, Flamm, Bruce, J. Appld. Phys. 1985, vol. 58 (6) pp. 2135-2144.
Carrington, Milverton, Sarre, Molecular Physics, 1978, vol. 25 (6) pp. 1505-1521.
Brown, Godrey, McGilvery, Crofts, Chem. Phys. Lett. 1981, vol. 84 (3), pp. 437-439.
Leach, J. Chim, Phys. 1980 vol. 77 (7/8) pp. 585-588.
Maier, Marthaler, Misev, Thommen, in Molecular Ions, Ed. Berkowitz Groeneveld, Plenum Press, 1983, pp. 125-152.
Klapstein, Maier, Misev, in Molecular Ions, Ed. Miller and Bondybey, North Holland, 1983, pp. 175, 200.
Figger, Phys. Tev. Lett. 1984 vol. 52, p. 906.
Holmes, Mayer, Mommers, J. Am. Chem. Soc. 1991, vol. 113 (24) pp. 9405-9406.

*Primary Examiner*—Bruce C. Anderson
*Attorney, Agent, or Firm*—Chilton, Alix & Van Kirk

[57] ABSTRACT

A collision cell for observing the emission spectrum of ions. The substantially enclosed collision cell (8) is bounded by a wall (46), the wall having an entrance aperture (47) and an exit aperture (29) through which an ion beam (5) may be passed to traverse the collision cell, and has an observation region (15) therein adjacent to the entrance aperture and a first window (22) in the wall through which radiation generated in the observation region may pass, and, disposed adjacent to the exit aperture and in communication with the observation region, an exit region (16) comprising radiation-trapping means for minimizing the transmission to the first window of radiation generated in the exit region. The collision cell may be incorporated in a conventional mass spectrometer.

22 Claims, 3 Drawing Sheets

MASS SPECTROMETER HAVING MEANS FOR OBSERVING THE RADIATION EMITTED WHEN IONS COLLIDE WITH A TARGET GAS

This invention relates to a mass spectrometer having means for observing the optical emission spectra resulting from the interaction of a mass selected ion beam with a collision target gas. It is especially applicable to observation of the optical spectra from polyatomic organic ions. The invention also provides collision cell means which can be fitted to a conventional mass spectrometer to enable the emission spectrum of ions to be observed.

Although the emission spectra of ions have been studied for many years, most observations have been carried out for ions of simple structure and of low molecular weight, often produced in discharges or by photoionization. There are few reports of the emission spectra of polyatomic ions generated by other means such as the direct electron beam ionization of a gaseous sample.

It is of course difficult to study both the emission and adsorption spectra of molecular ions because the classical techniques used for neutral molecules are not usually successful with ionic species. Leach (J. Chim. Phys. 1980 vol 77 (7/8) pp 585–8) points out the difficulty of creating sufficiently high ion densities for sufficiently long durations to allow a spectrum to be recorded by conventional methods. Effects such as ion-electron recombination, ion-molecule reactions and spontaneous dissociation of the electronic excited states of many ions also seriously reduce the chance of recording the emission spectrum by conventional means. However, Maier, Marthler, Miser and Thommen (in Molecular Ions, Geometric and Electronic Structures, Ed. Berkowitz, Groeneveld, Plenum Press, N.Y., 1983) have described apparatus in which a sample gas introduced into a collision region within a vacuum system is bombarded with electrons of typically 20–40 eV to ionize the sample, and the emission of optical radiation by the sample ions so formed is detected by a monochromator and photomultiplier. Emission spectra having bands in the 250 nm–900 nm region of a wide range of simple organic cations (chiefly halogenated species up to about $C_{10}$) have been reported.

Klapstein, Maier and Misev (in Molecular Ions, Structure and Chemistry, Ed. Miller and Bondybey, North Holland, 1983, pp 175–200) report a crossed-beam apparatus wherein a supersonic jet of a mixture of the sample gas and helium is directed perpendicularly across a collimated electron beam within an evacuated enclosure. Optical radiation is extracted along an axis mutually perpendicular to the molecular and electron beams and enters a monochromator and photomultiplier.

Hatada, Fujita, Nakai, and Hirota (JAERI,Issue 5026 pp 1–5) fitted a quartz window to the ion source of an electron-impact ionization mass spectrometer and observed the emission spectrum of species such as $N_2^+$ and $CO^+$ upon introduction of nitrogen, nitrogen oxides, carbon monoxide, low molecular weight hydrocarbons and acetone. They concluded that it was impossible to observe emissions from complex ions in the excited state because such ions often revert to their ground states non-radiatively. They also observed that the emissions from the fragment molecules formed by dissociation were too strong, and recommended that in future work the concentration of such fragment molecules should be reduced by fast differential pumping.

Leventhal (in Gas Phase Ion Chemistry, Vol 3 ed. Michael T. Bowers Academic Press Inc. 1984 pp 309–355) describes results on the emission of light from excited products of charge exchange reactions. Optical radiation is analysed after passing from a collision cell in a single focusing mass spectrometer. Interest centres around the behaviour of simple mono to triatomic ions and target gases. Some similar work has also been described by Figger et al (Phys. Rev. Lett. Vol 52 1984 p906).

Holmes, Mayer and Mommers (J. Amer. Chem. Soc. 1991 vol 113(24) pp 9405–6 and Org. Mass Spectrom. 1992, vol 27 (4) pp537–539) observed emission spectra from $H_3^+$, $H_2^{+\cdot}$, $CH_3CHO^{+\cdot}$, $CH_2=CHOH^{+\cdot}$, $CH_2CH_2O^{+\cdot}$, $CH_3CH_2Cl^{+\cdot}$ and $CH_3ClCH_2^{+\cdot}$ produced by collisions between mass selected ion beams and target gases in the collision region between the magnetic sector and electrostatic sector of a conventional high-resolution double-focusing mass spectrometer. They demonstrated that the isomeric ions $CH_3CH_2Cl^{+\cdot}$ and $CH_3ClCH_2^{+\cdot}$, and $CH_3CHO^{+\cdot}$, $CH_2=CHOH^{+\cdot}$ and $CH_2CH_2O^{+\cdot}$ could be distinguished by their emission spectra.

However, the simple design of the collision cell used in this work was such that only relatively long-lived excited states (0.1 μs) could be studied, and emissions from target gas and the metal surfaces of the cell caused by collisions with scattered ions were troublesome.

It is an object of the present invention to provide an improved collision cell arrangement with means for observing the emission spectra of species within it which is suitable for use in a mass spectrometer. It is another object of the invention to provide a mass spectrometer incorporating such a collision cell arrangement.

The invention provides substantially enclosed collision cell means, bounded by a wall, said wall having entrance and exit apertures through which an ion beam may be passed to traverse said cell means, wherein said cell means comprises an observation region therein adjacent said entrance aperture and having a window in said wall through which radiation generated in said observation region may pass, and, disposed adjacent to said exit aperture and in communication with said observation region, an exit region comprising radiation-trapping means for minimizing the transmission to said window of radiation generated in said exit region.

Cell means according to the invention are typically disposed within the vacuum envelope of a mass spectrometer intended for collision induced dissociation studies and may replace a collision cell conventionally provided in any such instrument. A vacuum-tight window may be provided in the vacuum envelope to permit radiation emerging from the window in the collision cell to leave the vacuum envelope and pass into a suitable optical monochromator and detector. In this way the optical spectra of species undergoing spectroscopic transitions in the observation region of the cell means can be recorded. Preferably both windows are of quartz and are connected by a light-tight tube with a highly polished interior surface.

As in conventional tandem mass spectrometry experiments, ions entering the collision cell means collide with molecules of the target gas. The emission spectrum observed arises from species, charged or neutral, resulting from interactions of the mass selected ion beam with the target gas within the cell or (see below) within a zone before the observation cell. By passing the ion beam from the observation region of the cell means into the exit region which comprises radiation-trapping means, interference to the desired collision induced spectrum is greatly reduced because radiation resulting from the impact of the ion beam with the wall of the collision cell means in the vicinity of the cell exit aperture is absorbed by the radiation-trapping means provided in the exit region. The radiation-trapping means may conveniently comprise a blackened coating on the wall of the cell means in the exit region (for example, a coating of carbon particles applied to the surfaces by painting a solution of colloidal graphite on them during assembly). Preferably the observation region of the cell means opposite to the window comprises a highly polished concave surface, for example, hemicylindrical.

The invention further provides a mass spectrometer comprising at least an ion source, a mass analyzer and/or energy analyzer for providing a mass and/or energy filtered beam of ions, collision cell means as defined above disposed in the path of said beam of ions, and spectroscopic means for recording at least a part of the spectrum of radiation passing through the window in the collision cell means. Conveniently the mass spectrometer will further comprise an ion detector and at least one further mass, momentum and/or energy analyzer disposed between the collision cell means and the ion detector to enable complete tandem mass spectrometry experiments to be performed while observing the emission spectrum of species in the collision cell means.

It will be appreciated that the species whose emission spectrum is observed need not be formed in the observation region itself. A second, conventional, collision cell may be disposed in the path of the ion beam before it reaches the collision cell means of the invention. A conventional collision cell means any design of collision cell suitable for allowing an ion beam to undergo collisions therein, for example with a target gas contained therein. Ions in the main beam may undergo collisions in the second cell but undergo the spectroscopic transition some time later as they pass through the cell means according to the invention so that their emission spectrum can be observed. Using a conventional tandem mass spectrometer, this method is appropriate for species whose excited state has a lifetime of $>0.1$ $\mu S$ or so. It is also possible to vary the energy of the collisions and the transit time of ions between the cells by adjusting the potentials applied to the cells themselves. Typically the radiation observed will be in the UV/visible range, from 180–680 nm, but other wavelength ranges may be used providing suitably transparent windows are employed. Any suitable monochromator and photomultiplier may be used to record the emission spectrum.

An embodiment of the invention will now be described in greater detail by way of example only and with reference to the figures, in which.

Figure 1:
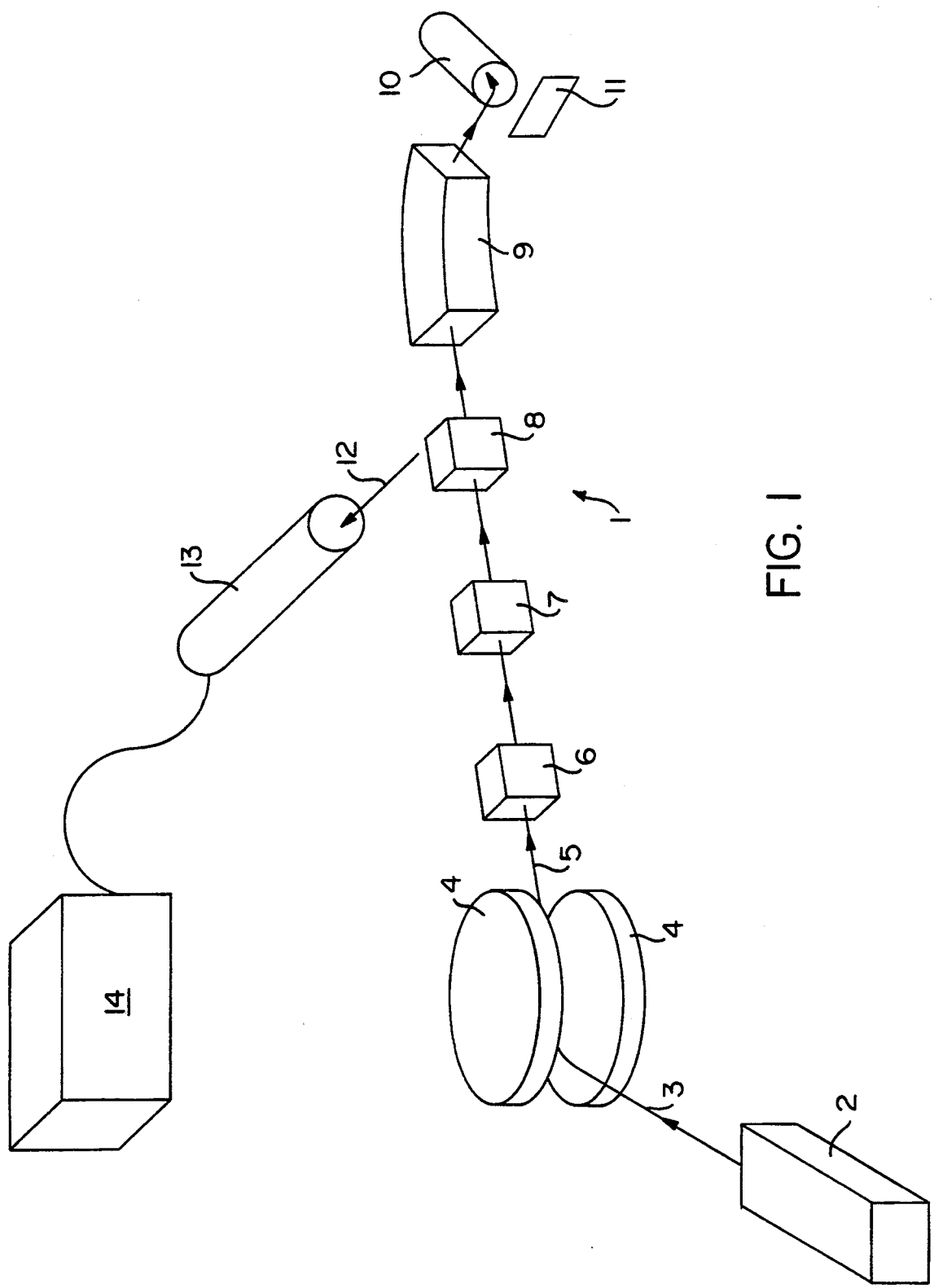
FIG. 1 is a schematic diagram of a mass spectrometer incorporating a collision cell according to the invention.

Referring to FIG. 1, a mass spectrometer generally indicated by 1 comprises an ion source 2 which generates a beam of ions 3 which are momentum dispersed by a magnetic sector analyzer 4 to produce a momentum-selected ion beam 5. Two conventional collision cells 6, 7 are provided in the path of the ion beam 5 and a collision cell 8 according to the invention is disposed after them.

After emerging from the collision cell 8 the ion beam passes into an electrostatic energy analyzer 9 as in a conventional double-focusing spectrometer. A deflection electrode 11 is provided to deflect the ion beam emerging from the electrostatic analyzer 9 into an off-axis ion detector 10.

Species undergoing spectroscopic transitions in the observation region of the collision cell means 8 emit radiation 12 which passes through a monochromator and photodetector 13 which are controlled by a spectroscopic data acquisition system and controller 14 so that the spectrum of the radiation may be recorded. Typically, the UV/visible emission spectrum from about 180–680 nm would be recorded but other wavelength ranges may be used with suitable spectroscopic equipment.

Figure 2:
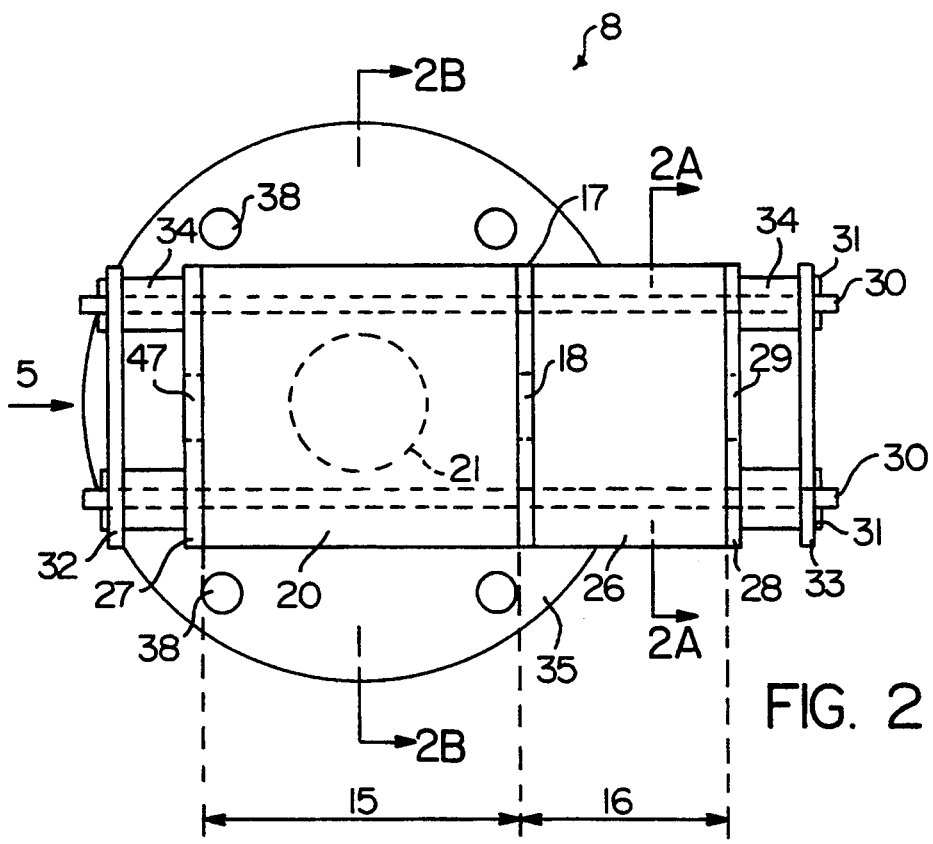
FIG. 2 is a side elevation view of a collision cell according to the invention.
Figure 2A:
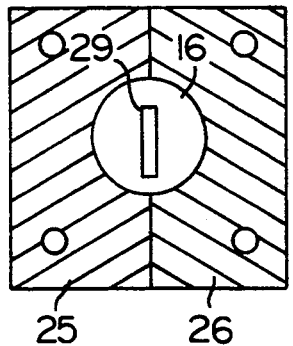
FIG. 2A is a cross-sectional view of the collision cell taken in plane 2A—2A of FIG. 2.
Figure 2B:
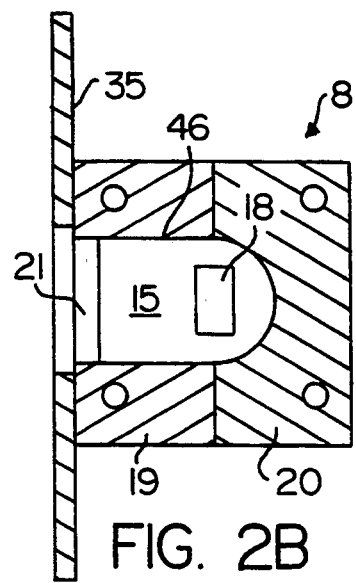
FIG. 2B is a cross-sectional view taken in plane 2B—2B of of FIG. 2.
Figure 3:
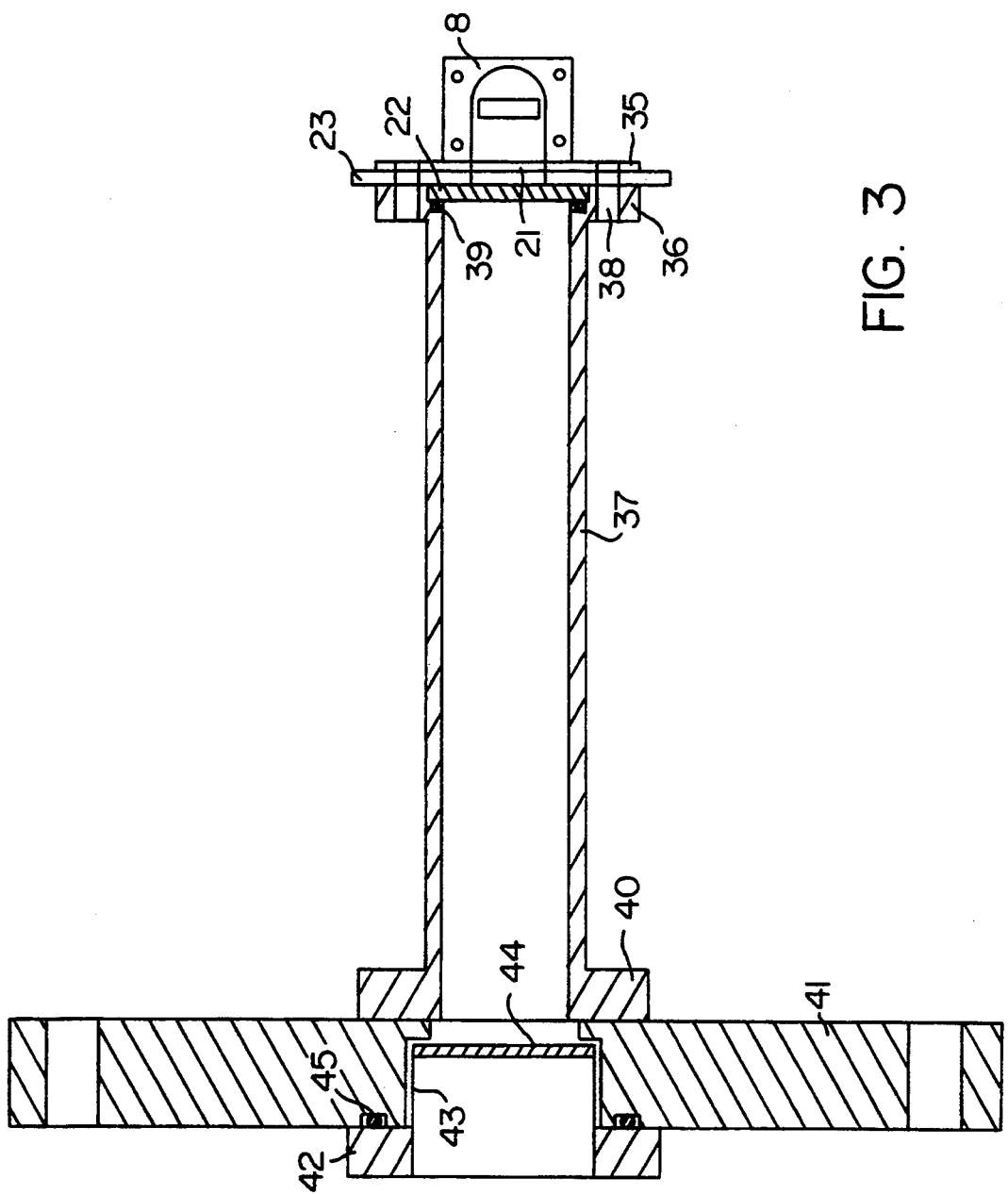
FIG. 3 is a drawing showing how the collision cell of FIG. 2 is mounted in a mass spectrometer according to the invention.

FIGS. 2A and 2B illustrate the construction of a collision cell 8 suitable for use in the spectrometer of FIG. 1. It comprises an observation region 15 and an exit region 16 disposed so that the ion beam 5 passes first through the observation region and then through the exit region. The two regions are separated by a slit plate 17 which comprises a rectangular aperture 18 which provides communication between them, so that ions may pass from the observation region to the exit region. The aperture 18 is large enough to ensure that the ion beam passes through it without striking the plate 17. The observation region 15 is formed in a rectangular block comprising an observation cell body portion 19 and an observation cell cover portion 20. A rectangular section trough is machined in the body portion 19 to define the wall 46 which bounds the collision cell means and a circular hole 21 is made in its base as illustrated in FIG. 2. Hole 21 is closed after assembly by the window 22 and insulator 23 (FIG. 3). The cover portion 20 comprises a machined trough of hemicylindrical cross-section and is fitted as shown in FIG. 2B.

The inside surfaces of the body portion 19 and cover portion 20 are highly polished to ensure that radiation generated in the observation region 15 is reflected through the hole 21. The exit portion 16 comprises an exit region body portion 25 and an exit region cover portion 26 machined as shown to define a region into which the ions pass through the aperture 18 in the slit plate 17. The inside surfaces of the body and cover portions 25 and 26 are blackened by a deposit of fine carbon particles thereby providing radiation-trapping means which prevent any radiation emitted in the exit region from being reflected back into the observation region. The carbon particles may be applied by painting a colloidal solution of graphite on the surfaces and evaporating the solvent.

The ends of the observation region 15 and the exit region 16 are closed by slit plates 27 and 28 respectively. An entrance aperture 47 is formed in the slit plate 27 and an exit aperture 29 is formed in the slit plate 28. Apertures 47 and 29 are both smaller than the aperture 18 in plate 17 to ensure that the ion beam 5 does not strike the surface of the plate 17 inside the observation region 15.

The four portions 19, 20, 25 and 26 and the three slit plates 17, 27 and 28 are assembled on four ceramic rods 30 which are fitted with spring washers and circlips 31 to tension the assembly. Two focusing electrodes 32, 33, electrically insulated from the cell by the tubular insulators 34, are fitted to the ends of the cell on the rods 30 as shown. These are used to ensure proper focusing of the ion beam as it passes through the collision cell as in a conventional mass spectrometer collision cell.

FIG. 3 illustrates how the collision cell means shown in FIG. 2 may be mounted on the vacuum envelope of the mass spectrometer. The observation region body portion 19 is attached to a circular support plate 35 which is in turn bolted to a flange 36 on a hollow support tube 37, but separated from it by the PTFE insulator 23. Four bolts (not shown) are fitted through insulated bushes in the holes 38 in the support plate 35. This arrangement permits the cell means 8 to be floated at any potential (to control the energy of the ion-molecule collisions inside it) while the support tube 37 remains at ground potential. A quartz window 22 is fitted on an 'O'-ring seal in such a way that the cell means 8 is substantially gas-tight (except of course for the apertures in the entrance and exit slit plates 27 and 28), but optical radiation can pass from the collision region 24 through the hole 21 (and similar holes in the insulator 23 and support plate 35) through the window 22 into the interior of the support tube 37.

A flange 40 is attached to the end of the tube 37, permitting it to be bolted to a vacuum flange 41 which is adapted to fit a port on the vacuum envelope of the mass spectrometer. The position of this port and the length of the tube 37 are selected to position the apertures in the slit plates 27, 17 and 28 in the path of the ion beam of the mass spectrometer. To ensure efficient analysis of the radiation the support tube should be as short as possible. The centre of the vacuum flange 41 is bored out to take a view port 42 which comprises a short tube 43 carrying a quartz window 44 as shown. The view port flange is bolted to the vacuum flange 41 and sealed by an 'O'-ring 45.

The interior of the support tube 37 is highly polished to ensure maximum transmission of optical radiation from the window 22 to the window 44. Holes are also provided in the tube 37 to ensure that its interior is maintained at the same pressure as the interior of the mass spectrometer vacuum envelope.

A conventional optical spectrometer (shown schematically at 13 in FIG. 1) is disposed to receive the radiation which passes through the window 44. In this way the spectrum of the radiation emitted from species undergoing spectroscopic transitions in the observation region 15 can be determined without interference from radiation resulting from any collision of the ion beam or scattered species with the surfaces of the collision cell itself. This is achieved by allowing the beam to pass into the exit region of the cell which is provided with radiation trapping means to prevent the latter radiation reaching the spectrometer 13.

In use, a target gas may be introduced into the collision region 24 of the cell means 8. A mass-selected beam of ions 5 enters the cell and ions in it undergo fragmentation and/or collisional excitation. Collisionally excited species may then emit radiation 12 which passes out of the cell into the spectrometer 13. In the embodiment illustrated, the radiation leaving the cell means 8 is detected in the plane in which the momentum dispersion of the ion beam 5 takes place because it is easier in practice to modify a mass spectrometer of conventional design in this way. However, it is within the scope of the invention to arrange the windows 22 and 44 and the optical spectrometer 13 to detect radiation emitted perpendicularly to the dispersion plane of the mass spectrometer. The embodiment of FIG. 1 shows two conventional collision cells 6, 7 in addition to the cell means 8 according to the invention. These conventional cells can be used for a variety of different experiments. For example, ions may be collisionally excited in the cell 7 and radiation emitted be observed in the cell 8 (which is operated without a target gas). Similarly, species produced in the cells 6 or 7 could be collisionally activated in the cell 8. Further, the energy of ions, and their transit times through the entire collision region, can be varied by applying different potentials to the cells, as in conventional tandem mass spectometry experiments. However, it is within the scope of the invention to provide only the cell means 8.

It will also be appreciated that the species whose emission spectra is monitored will exit from the collision cell means 8 and can be further mass or energy analyzed in the mass spectrometer as in conventional tandem mass spectrometers or mass and ion-kinetic energy spectrometers (MIKES spectrometers). The conventional two-sector spectrometer as shown in FIG. 1 provides an electrostatic energy analyzer 9 and ion detector 10, thereby allowing MIKES type spectra to be produced, but it is within the scope of the invention to provide further magnetic sector analyzers and/or electrostatic analyzers in place of the electrostatic sector 9. The magnetic sector analyzer 4 may also be replaced by a double-focusing mass analyzer comprising both electrostatic and magnetic sectors to provide high resolution mass filtering of the beam 5.

We claim:

1. A substantially enclosed collision cell comprising:
a wall bounding said collision cell;
an entrance aperture and an exit aperture in said wall, through which an ion beam may be passed to traverse said collision cell;
an observation region in said collision cell adjacent to said entrance aperture;
a first window in said wall through which radiation generated in said observation region may pass; and
an exit region in said collision cell adjacent to said exit aperture and in communication with said observation region, said exit region comprising radiation-trapping means for minimizing the transmission to said first window of radiation generated in said exit region.

2. A collision cell as claimed in claim 1 wherein said radiation-trapping means comprises a blackened coating on the wall of said collision cell in said exit region.

3. A collision cell as claimed in claim 2 wherein said blackened coating comprises carbon applied by painting a solution of colloidal graphite on said wall during assembly of said cell.

4. A collision cell as claimed in claim 1 wherein the wall of said cell in said observation region opposite to said first window comprises a highly polished concave surface.

5. A spectrometer comprising:
a vacuum envelope;

a substantially enclosed collision cell disposed in said vacuum envelope, said collision cell comprising:

a wall bounding said collision cell;

an entrance aperture and an exit aperture in said wall, through which an ion beam may be passed to traverse said collision cell;

an observation region in said collision cell adjacent to said entrance aperture;

a first window in said wall through which radiation generated in said observation region may pass; and an exit region in said collision cell adjacent to said exit aperture and in communication with said observation region, said exit region comprising radiation-trapping means for minimizing the transmission to said first window of radiation generated in said exit region; said spectrometer further comprising:

means for passing a beam of ions from an ion source through said entrance and exit apertures; and a second window in said vacuum envelope through which may pass radiation which has passed through said first window.

6. A spectrometer as claimed in claim 5 wherein said first and second windows are connected by a light-tube having a highly polished interior surface.

7. A spectrometer as claimed in claim 5 further comprising a monochromator and a detector to receive at least some of the radiation passing through said first and second windows to record the optical spectrum of species undergoing spectroscopic transitions in said observation region.

8. A spectrometer as claimed in claim 5 wherein said first and second windows are made of quartz which transmits radiation of wavelengths at least in the range 180–680 nm.

9. A spectrometer as claimed in claim 5 wherein said means for passing a beam of ions comprises a mass and/or energy analyzer for providing a mass and/or energy filtered beam of ions from said ion source.

10. A spectrometer as claimed in claim 9 further comprising an ion detector disposed to receive ions leaving said exit aperture and at least one further mass, momentum and/or energy analyzer disposed between said collision cell and said ion detector.

11. A spectrometer as claimed in claim 5 further comprising a conventional collision cell disposed in the path of the ion beam before it reaches said collision cell, whereby ions undergo collisions in said conventional collision cell and undergo spectroscopic transitions during their subsequent passage through said collision cell.

12. A spectrometer as claimed in claim 11 wherein potentials are applied to said collision cell and to said conventional collision cell to adjust the energy of the collisions in said cells and/or the transit times of the ions through said cells.

13. A substantially enclosed collision cell comprising:

a wall bounding said collision cell;

an entrance aperture and an exit aperture in said wall, through which an ion beam may be passed to traverse said collision cell;

an observation region in said collision cell adjacent to said entrance aperture;

a first window in said wall through which radiation generated in said observation region may pass; and an exit region in said collision cell adjacent to said exit aperture and in communication with said observation region, said exit region comprising radiation-trapping means for minimizing the transmission to said first window of radiation generated in said exit region;

wherein said radiation-trapping means comprises a blackened coating on the wall of said collision cell in said exit region; and the wall of said collision dell in said observation region opposite to said first-window comprises a highly polished concave surface.

14. A spectrometer comprising:

a vacuum envelope;

a substantially enclosed collision cell disposed in said vacuum envelope, said collision cell comprising:

a wall bounding said collision cell;

an entrance aperture and an exit aperture in said wall, through which an ion beam may be passed to traverse said collision cell;

an observation region in said collision cell adjacent to said entrance aperture;

a first window in said wall through which radiation generated in said observation region may pass; and an exit region in said collision cell adjacent to said exit aperture and in communication with said observation region, said exit region comprising radiation-trapping means for minimizing the transmission to said first window of radiation generated in said exit region;

wherein said radiation-trapping means comprises a blackened coating on the wall of said collision cell in said exit region; and the wall of said collision cell in said observation region opposite to said first window comprises a highly polished concave surface; said spectrometer further comprising:

means for passing a beam of ions from an ion source through said entrance and exit apertures;

a second window in said vacuum envelope through which may pass radiation which has passed through said first window; and a monochromator and a detector to receive at least some of the radiation passing through said first and second windows to record the optical spectrum of species undergoing spectroscopic transitions in said observation region.

15. A spectrometer as claimed in claim 14 wherein said means for passing a beam of ions comprises a mass and/or energy analyzer for providing a mass and/or energy filtered beam of ions from said ion source.

16. A spectrometer as claimed in claim 15 further comprising an ion detector disposed to receive ions leaving said exit aperture and at least one further mass, momentum and/or energy analyzer disposed between said collision cell and said ion detector.

17. A spectrometer as claimed in claim 14 further comprising a conventional collision cell disposed in the path of the ion beam before it reaches said collision cell, whereby ions undergo collisions in said conventional collision cell and undergo spectroscopic transitions during their subsequent passage through said collision cell.

18. A spectrometer as claimed in claim 17 wherein potentials are applied to said collision cell and to said conventional collision cell to adjust the energy of the collisions in said cells and/or the transit times of the ions through said cells.

19. A spectrometer comprising:

a vacuum envelope;

a substantially enclosed collision cell disposed in said vacuum envelope, said collision cell comprising:

a wall bounding said collision cell;

an entrance aperture and an exit aperture in said wall, through which an ion beam may be passed to traverse said collision cell;

an observation region in said collision cell adjacent to said entrance aperture;

a first window in said wall through which radiation generated in said observation region may pass; and an exit region in said collision cell adjacent to said exit aperture and in communication with said observation region, said exit region comprising radiation-trapping means for minimizing the transmission to said first window of radiation generated in said exit region; said spectrometer further comprising:

means for passing a beam of ions from an ion source through said entrance and exit apertures, said passing means comprising a mass and/or energy analyser for providing a mass and/or energy filtered beam of ions from said ion source;

a second window in said vacuum envelope through which may pass radiation which has passed through said first window; and a conventional collision cell disposed in the path of the ion beam before it reaches said collision cell, whereby ions undergo collisions in said conventional collision cell and undergo spectroscopic transitions during their subsequent passage through said collision cell.

20. A spectrometer as claimed in claim 19 further comprising a monochromator and a detector to receive at least some of the radiation passing through said first and second windows to record the optical spectrum of species undergoing spectroscopic transitions in said observation region.

21. A spectrometer as claimed in claim 19 further comprising an ion detector disposed to receive ions leaving said exit aperture and at least one further mass, momentum and/or energy analyzer disposed between said collision cell and said ion detector.

22. A spectrometer as claimed in claim 19 wherein potentials are applied to said collision cell and to said conventional collision cell to adjust the energy of the collisions in said cells and/or the transit times of the ions through said cells.

* * * * *